US010036574B2

(12) United States Patent
Brereton et al.

(10) Patent No.: US 10,036,574 B2
(45) Date of Patent: Jul. 31, 2018

(54) DEVICES COMPRISING A HEAT SOURCE MATERIAL AND ACTIVATION CHAMBERS FOR THE SAME (71) Applicant: British American Tobacco (Investments) Limited, London (GB)

(72) Inventors: Simon Brereton, London (GB); Neil Litten, London (GB); Graham Plews, London (GB); Mark Forster, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 393 days.

(21) Appl. No.: 14/899,629

(22) PCT Filed: Jun. 27, 2014

(86) PCT No.: PCT/EP2014/063785
§ 371 (c)(1),
(2) Date: Dec. 18, 2015

(87) PCT Pub. No.: WO2014/207250
PCT Pub. Date: Dec. 31, 2014

(65) Prior Publication Data
US 2016/0146506 A1 May 26, 2016

(30) Foreign Application Priority Data

Jun. 28, 2013 (GB) .................................. 1311620.7

(51) Int. Cl.
*A24F 47/00* (2006.01)
*F24J 1/00* (2006.01)
(Continued)

(52) U.S. Cl.
CPC ............... *F24J 1/00* (2013.01); *A24F 47/006* (2013.01); *A61F 7/034* (2013.01); *A61M 11/047* (2014.02);
(Continued)

(58) Field of Classification Search
CPC ........... A24F 47/00; A61M 15/06; A61F 7/03; F28D 20/02
(Continued)

(56) References Cited

U.S. PATENT DOCUMENTS 2,462,563 A  2/1949  Seyforth
2,689,150 A  9/1954  Corce
(Continued)

FOREIGN PATENT DOCUMENTS

AT   262137   5/1968
AT   306224   3/1973
(Continued)

OTHER PUBLICATIONS

UKIPO Search Report dated Jan. 17, 2013 for UK Patent Application No. GB1216621.1 filed Sep. 18, 2012.
(Continued)

*Primary Examiner* — Gregory Huson
*Assistant Examiner* — Nikhil Mashruwala
(74) *Attorney, Agent, or Firm* — Patterson Thuente Pedersen, P.A.

(57) ABSTRACT

A device is provided comprising a heat source material which is a phase change material and which undergoes an exothermic phase change upon activation by an activating agent to generate heat, a heat source chamber holding the heat source and an activation chamber providing the activating agent, and a barrier separating the interior of the heat source chamber from the interior of the activation chamber, wherein the activation chamber is deformable and wherein
(Continued)

deformation of the activation chamber causes rupture of the barrier to allow contact between the activating agent and the heat source material. Embodiments also provide an activation chamber for use in the device and comprising an activating agent to trigger activation of a heat source material.

20 Claims, 4 Drawing Sheets

(51) Int. Cl.
*A61M 15/06* (2006.01)
*A61M 11/04* (2006.01)
*A61F 7/03* (2006.01)
*F28D 20/02* (2006.01)
*A61F 7/02* (2006.01)

(52) U.S. Cl.
CPC ..... *A61M 15/06* (2013.01); *A61F 2007/0276* (2013.01); *A61F 2007/0292* (2013.01); *F28D 20/028* (2013.01)

(58) Field of Classification Search
USPC .............................. 126/263.07, 204; 44/266
See application file for complete search history.

(56) References Cited

U.S. PATENT DOCUMENTS

| | | |
|---|---|---|
| 2,888,208 A | 5/1959 | Fedit |
| 3,040,991 A | 6/1962 | Fedit |
| 3,043,524 A | 7/1962 | Boris |
| 3,258,015 A | 6/1966 | Herbert et al. |
| 3,289,949 A | 12/1966 | Roth |
| 3,347,231 A | 10/1967 | Chang |
| 3,522,806 A | 8/1970 | Szekely |
| 3,647,143 A | 3/1972 | Gauthier et al. |
| 3,658,059 A | 4/1972 | Steil |
| 3,733,010 A | 5/1973 | Riccio |
| 3,856,185 A | 12/1974 | Riccio |
| 3,864,326 A | 2/1975 | Babington et al. |
| 3,913,843 A | 10/1975 | Cambio, Jr. |
| 3,943,942 A | 3/1976 | Anderson |
| 4,149,548 A | 4/1979 | Bradshaw |
| 4,284,089 A | 8/1981 | Ray |
| 4,299,274 A | 11/1981 | Campbell et al. |
| 4,299,355 A | 11/1981 | Hakkinen |
| 4,303,541 A | 12/1981 | Wasel-Nielen et al. |
| 4,393,884 A | 7/1983 | Jacobs |
| 4,412,930 A | 11/1983 | Koike et al. |
| 4,429,835 A | 2/1984 | Brugger et al. |
| 4,694,841 A | 9/1987 | Esparza |
| 4,746,067 A | 5/1988 | Svoboda |
| 4,765,348 A | 8/1988 | Honeycutt |
| 4,771,795 A | 9/1988 | White et al. |
| 4,776,353 A | 10/1988 | Lilja et al. |
| 4,819,665 A | 4/1989 | Roberts et al. |
| 4,827,950 A | 5/1989 | Banerjee et al. |
| 4,892,109 A | 1/1990 | Strubel |
| 4,907,606 A | 3/1990 | Lilja |
| 4,913,168 A | 4/1990 | Potter et al. |
| 4,917,119 A | 4/1990 | Potter et al. |
| 4,917,120 A | 4/1990 | Hill |
| 4,924,883 A | 5/1990 | Perfetti et al. |
| 4,938,236 A | 7/1990 | Banerjee et al. |
| 4,941,483 A | 7/1990 | Ridings et al. |
| 4,947,874 A | 8/1990 | Brooks et al. |
| 4,955,399 A | 9/1990 | Potter et al. |
| 5,019,122 A | 5/1991 | Clearman et al. |
| 5,020,509 A | 6/1991 | Suzuki et al. |
| 5,040,552 A | 8/1991 | Schleich et al. |
| 5,042,509 A | 8/1991 | Banerjee et al. |
| 5,060,667 A | 10/1991 | Strubel |
| 5,060,671 A | 10/1991 | Counts et al. |
| 5,076,292 A | 12/1991 | Sensabaugh et al. |
| 5,080,115 A | 1/1992 | Templeton |
| 5,093,894 A | 3/1992 | Deevi et al. |
| 5,095,921 A | 3/1992 | Losee et al. |
| 5,097,850 A | 3/1992 | Braunshteyn et al. |
| 5,099,861 A | 3/1992 | Clearman et al. |
| 5,105,831 A | 4/1992 | Banerjee et al. |
| 5,119,834 A | 6/1992 | Shannon et al. |
| 5,133,368 A | 7/1992 | Neumann |
| 5,143,048 A | 9/1992 | Cheney, III |
| 5,144,962 A | 9/1992 | Counts et al. |
| 5,146,934 A | 9/1992 | Deevi et al. |
| 5,159,940 A | 11/1992 | Hayward et al. |
| 5,167,242 A | 12/1992 | Turner et al. |
| 5,179,966 A | 1/1993 | Losee et al. |
| 5,188,130 A | 2/1993 | Hajaligol et al. |
| 5,224,498 A | 7/1993 | Deevi |
| 5,230,715 A | 7/1993 | Iizuna |
| 5,235,992 A | 8/1993 | Sensabaugh, Jr. |
| 5,261,424 A | 11/1993 | Sprinkel |
| 5,269,327 A | 12/1993 | Counts et al. |
| 5,285,798 A | 2/1994 | Banerjee et al. |
| 5,293,883 A | 3/1994 | Edwards |
| 5,305,733 A * | 4/1994 | Walters ............... A61F 7/03 126/204 |
| 5,312,046 A | 5/1994 | Knoch et al. |
| 5,327,915 A | 7/1994 | Porenski et al. |
| 5,345,951 A | 9/1994 | Serrano et al. |
| 5,357,984 A | 10/1994 | Farrier et al. |
| 5,369,723 A | 11/1994 | Counts et al. |
| 5,396,911 A | 3/1995 | Casey et al. |
| 5,400,808 A | 3/1995 | Turner et al. |
| 5,408,574 A | 4/1995 | Deevi et al. |
| 5,415,186 A | 5/1995 | Casey et al. |
| 5,443,560 A | 8/1995 | Deevi et al. |
| 5,454,363 A | 10/1995 | Sata |
| 5,461,695 A | 10/1995 | Knoch |
| 5,474,059 A | 12/1995 | Cooper |
| 5,483,953 A | 1/1996 | Cooper |
| 5,501,236 A | 3/1996 | Hill et al. |
| 5,511,538 A | 4/1996 | Haber |
| 5,517,981 A | 5/1996 | Taub et al. |
| 5,534,020 A | 7/1996 | Cheney, III |
| 5,538,020 A | 7/1996 | Farrier |
| 5,549,906 A | 8/1996 | Santus |
| 5,564,442 A | 10/1996 | MacDonald et al. |
| 5,593,792 A | 1/1997 | Farrier et al. |
| 5,613,505 A | 3/1997 | Campbell et al. |
| 5,645,749 A | 7/1997 | Wang |
| 5,649,554 A | 7/1997 | Sprinkel et al. |
| 5,659,656 A | 8/1997 | Das |
| 5,687,912 A | 11/1997 | Denyer |
| 5,699,786 A | 12/1997 | Oshima et al. |
| 5,711,292 A | 1/1998 | Hammarlund |
| 5,736,110 A | 4/1998 | Angelillo et al. |
| 5,778,899 A | 7/1998 | Saito et al. |
| 5,819,756 A | 10/1998 | Mielordt |
| 5,845,649 A | 12/1998 | Saito et al. |
| 5,865,186 A | 2/1999 | Volsey |
| 5,921,233 A | 7/1999 | Gold et al. |
| 5,935,486 A | 8/1999 | Bell et al. |
| 5,938,125 A | 8/1999 | Ritsche et al. |
| 5,984,953 A * | 11/1999 | Sabin ................ A61F 7/03 607/108 |
| 6,000,394 A | 12/1999 | Blaha-Schnabel |
| 6,041,790 A | 3/2000 | Smith et al. |
| 6,053,176 A | 4/2000 | Adams et al. |
| 6,079,405 A | 6/2000 | Justo |
| 6,085,741 A | 7/2000 | Becker |
| 6,089,857 A | 7/2000 | Matsuura et al. |
| 6,113,078 A | 9/2000 | Rock |
| 6,116,231 A * | 9/2000 | Sabin ................ A61F 7/03 126/204 |
| 6,129,080 A | 10/2000 | Pitcher et al. |
| 6,158,676 A | 12/2000 | Hughes |
| 6,164,287 A | 12/2000 | White |
| 6,178,963 B1 | 1/2001 | Baik |
| 6,209,457 B1 | 4/2001 | Kenworthy et al. |

(56) References Cited

U.S. PATENT DOCUMENTS

| | | | |
|---|---|---|---|
| 6,223,745 B1 | 5/2001 | Hammarlund et al. | |
| 6,230,703 B1 | 5/2001 | Bono | |
| 6,234,459 B1 | 5/2001 | Rock | |
| 6,244,573 B1 | 6/2001 | Rock | |
| 6,248,257 B1 | 6/2001 | Bell et al. | |
| 6,267,110 B1 | 7/2001 | Tenenboum et al. | |
| 6,283,116 B1 | 9/2001 | Yang | |
| 6,289,889 B1* | 9/2001 | Bell | A61F 7/03 126/263.07 |
| 6,347,789 B1 | 2/2002 | Rock | |
| 6,427,878 B1 | 8/2002 | Greiner-Perth et al. | |
| 6,595,209 B1 | 7/2003 | Rose et al. | |
| 6,598,607 B2 | 7/2003 | Adiga et al. | |
| 6,644,383 B2* | 11/2003 | Joseph | B65D 81/3484 126/263.01 |
| 6,648,306 B2 | 11/2003 | Rock | |
| 6,669,176 B2 | 12/2003 | Rock | |
| 6,708,846 B1 | 3/2004 | Fuchs et al. | |
| 6,723,115 B1 | 4/2004 | Daly | |
| 6,761,164 B2 | 7/2004 | Amirpour et al. | |
| 6,769,436 B2 | 8/2004 | Horian | |
| 6,799,572 B2 | 10/2004 | Nichols et al. | |
| 6,803,545 B2 | 10/2004 | Blake et al. | |
| 6,827,080 B2* | 12/2004 | Fish | A61F 7/03 126/263.01 |
| 6,886,556 B2 | 5/2005 | Fuchs | |
| 6,953,474 B2* | 10/2005 | Lu | A61F 7/03 607/108 |
| 6,968,888 B2 | 11/2005 | Kolowich | |
| 7,041,123 B2 | 5/2006 | Stapf et al. | |
| 7,077,130 B2 | 7/2006 | Nichols et al. | |
| 7,081,211 B2 | 7/2006 | Li et al. | |
| 7,088,914 B2 | 8/2006 | Whittle et al. | |
| 7,163,014 B2 | 1/2007 | Nichols et al. | |
| 7,234,459 B2 | 6/2007 | Del Bon | |
| 7,235,187 B2 | 6/2007 | Li et al. | |
| 7,290,549 B2 | 11/2007 | Banerjee et al. | |
| 7,303,328 B2 | 12/2007 | Faraldi et al. | |
| 7,335,186 B2 | 2/2008 | O'Neil | |
| 7,373,938 B2 | 5/2008 | Nichols et al. | |
| 7,434,584 B2 | 10/2008 | Steinberg | |
| 7,540,286 B2 | 6/2009 | Cross et al. | |
| 7,548,374 B2 | 6/2009 | Raymond et al. | |
| 7,581,540 B2 | 9/2009 | Hale et al. | |
| 7,581,718 B1 | 9/2009 | Chang | |
| 7,585,493 B2 | 9/2009 | Hale et al. | |
| 7,645,442 B2 | 1/2010 | Hale et al. | |
| 7,665,461 B2 | 2/2010 | Zierenberg et al. | |
| 7,832,397 B2 | 11/2010 | Lipowicz | |
| 7,834,295 B2 | 11/2010 | Sharma et al. | |
| 7,987,846 B2 | 8/2011 | Hale et al. | |
| 8,118,021 B2* | 2/2012 | Cho | A47J 36/28 126/263.01 |
| 8,156,944 B2 | 4/2012 | Han | |
| 8,342,184 B2 | 1/2013 | Inagaki et al. | |
| 8,365,742 B2 | 2/2013 | Hon | |
| 8,375,957 B2 | 2/2013 | Hon | |
| 2001/0042927 A1 | 11/2001 | Rock | |
| 2001/0054421 A1 | 12/2001 | Jaser et al. | |
| 2002/0043260 A1 | 4/2002 | Layer et al. | |
| 2002/0078951 A1 | 6/2002 | Nichols et al. | |
| 2002/0078955 A1 | 6/2002 | Nichols et al. | |
| 2002/0089072 A1 | 7/2002 | Rock | |
| 2002/0121624 A1 | 9/2002 | Usui | |
| 2003/0052196 A1 | 3/2003 | Fuchs | |
| 2003/0097164 A1 | 5/2003 | Stapf et al. | |
| 2003/0101984 A1 | 6/2003 | Li | |
| 2003/0105192 A1 | 6/2003 | Li et al. | |
| 2003/0106551 A1 | 6/2003 | Sprinkel, Jr. et al. | |
| 2003/0111637 A1 | 6/2003 | Li et al. | |
| 2003/0159702 A1 | 8/2003 | Lindell et al. | |
| 2003/0209240 A1 | 11/2003 | Hale et al. | |
| 2003/0217750 A1 | 11/2003 | Amirpour et al. | |
| 2003/0226837 A1 | 12/2003 | Blake et al. | |
| 2004/0065314 A1 | 4/2004 | Layer et al. | |
| 2004/0068222 A1 | 4/2004 | Brian | |
| 2004/0083755 A1 | 5/2004 | Kolowich | |
| 2004/0177849 A1 | 9/2004 | Del Bon | |
| 2004/0234699 A1 | 11/2004 | Hale et al. | |
| 2004/0234914 A1 | 11/2004 | Hale et al. | |
| 2004/0234916 A1 | 11/2004 | Hale et al. | |
| 2004/0255941 A1 | 12/2004 | Nichols et al. | |
| 2004/0261782 A1 | 12/2004 | Furumichi et al. | |
| 2005/0007870 A1 | 1/2005 | Faraldi et al. | |
| 2005/0016549 A1 | 1/2005 | Banerjee et al. | |
| 2005/0045193 A1 | 3/2005 | Yang | |
| 2005/0063686 A1 | 3/2005 | Whittle et al. | |
| 2005/0079166 A1 | 4/2005 | Damani et al. | |
| 2005/0133029 A1 | 6/2005 | Nichols et al. | |
| 2005/0196345 A1 | 9/2005 | Diederichs et al. | |
| 2005/0236006 A1 | 10/2005 | Cowan | |
| 2006/0027233 A1 | 2/2006 | Zierenberg et al. | |
| 2006/0032501 A1 | 2/2006 | Hale et al. | |
| 2006/0102175 A1 | 5/2006 | Nelson | |
| 2006/0118128 A1 | 6/2006 | Hoffman | |
| 2006/0137681 A1 | 6/2006 | Von Hollen et al. | |
| 2006/0191546 A1 | 8/2006 | Takano | |
| 2006/0196885 A1 | 9/2006 | Leach et al. | |
| 2007/0023043 A1 | 2/2007 | Von Hollen et al. | |
| 2007/0028916 A1 | 2/2007 | Hale et al. | |
| 2007/0031340 A1 | 2/2007 | Hale et al. | |
| 2007/0102533 A1 | 5/2007 | Rosell et al. | |
| 2007/0125362 A1 | 6/2007 | Ford et al. | |
| 2007/0131219 A1 | 6/2007 | Ford et al. | |
| 2007/0138207 A1 | 6/2007 | Bonney et al. | |
| 2007/0175476 A1 | 8/2007 | Lipowicz | |
| 2007/0204864 A1 | 9/2007 | Grychowski et al. | |
| 2007/0222112 A1 | 9/2007 | Christ et al. | |
| 2007/0283972 A1 | 12/2007 | Monsees et al. | |
| 2007/0289720 A1 | 12/2007 | Sunol et al. | |
| 2008/0038363 A1 | 2/2008 | Zaffaroni et al. | |
| 2008/0149118 A1 | 6/2008 | Oglesby et al. | |
| 2008/0156326 A1 | 7/2008 | Belcastro et al. | |
| 2008/0216828 A1 | 9/2008 | Wensley et al. | |
| 2008/0241255 A1 | 10/2008 | Rose et al. | |
| 2008/0257367 A1 | 10/2008 | Paterno et al. | |
| 2008/0276947 A1 | 11/2008 | Martzel | |
| 2008/0312674 A1 | 12/2008 | Chen et al. | |
| 2009/0015717 A1 | 1/2009 | Arnao et al. | |
| 2009/0071477 A1 | 3/2009 | Hale et al. | |
| 2009/0078711 A1 | 3/2009 | Farone et al. | |
| 2009/0090349 A1 | 4/2009 | Donovan | |
| 2009/0090351 A1 | 4/2009 | Sunol et al. | |
| 2009/0095287 A1 | 4/2009 | Emarlou | |
| 2009/0107492 A1 | 4/2009 | Ooida | |
| 2009/0114215 A1 | 5/2009 | Boeck et al. | |
| 2009/0151717 A1 | 6/2009 | Bowen et al. | |
| 2009/0162294 A1 | 6/2009 | Werner | |
| 2009/0180968 A1 | 7/2009 | Hale et al. | |
| 2009/0199843 A1 | 8/2009 | Farone et al. | |
| 2009/0217923 A1 | 9/2009 | Boehm et al. | |
| 2009/0230117 A1 | 9/2009 | Fernando et al. | |
| 2009/0260641 A1 | 10/2009 | Monsees et al. | |
| 2009/0260642 A1 | 10/2009 | Monsees et al. | |
| 2009/0280043 A1 | 11/2009 | Ferguson | |
| 2009/0301363 A1 | 12/2009 | Damani et al. | |
| 2009/0301471 A1 | 12/2009 | Stirzel | |
| 2009/0302019 A1 | 12/2009 | Selenski et al. | |
| 2010/0006092 A1 | 1/2010 | Hale et al. | |
| 2010/0025023 A1 | 2/2010 | Schmidt et al. | |
| 2010/0031968 A1 | 2/2010 | Sheikh et al. | |
| 2010/0043809 A1 | 2/2010 | Magnon | |
| 2010/0065052 A1 | 3/2010 | Sharma et al. | |
| 2010/0068154 A1 | 3/2010 | Sharma et al. | |
| 2010/0089381 A1 | 4/2010 | Bolmer et al. | |
| 2010/0181387 A1 | 7/2010 | Zaffaroni et al. | |
| 2010/0236546 A1 | 9/2010 | Yamada et al. | |
| 2010/0242974 A1 | 9/2010 | Pan | |
| 2010/0258585 A1 | 10/2010 | Jamison | |
| 2010/0300467 A1 | 12/2010 | Kuistila et al. | |
| 2010/0307518 A1 | 12/2010 | Wang | |
| 2010/0313901 A1 | 12/2010 | Fernando et al. | |
| 2011/0005535 A1 | 1/2011 | Xiu | |

(56) References Cited

U.S. PATENT DOCUMENTS

| | | | |
|---|---|---|---|
| 2011/0030671 A1 | 2/2011 | Ferguson et al. | |
| 2011/0192408 A1 | 8/2011 | Inagaki et al. | |
| 2011/0283458 A1 | 11/2011 | Gillette et al. | |
| 2011/0290266 A1 | 12/2011 | Koeller et al. | |
| 2012/0006342 A1 | 1/2012 | Rose et al. | |
| 2012/0006343 A1 | 1/2012 | Renaud et al. | |
| 2012/0132196 A1 | 5/2012 | Vladyslavovych | |
| 2012/0145189 A1 | 6/2012 | Knopow et al. | |
| 2013/0061861 A1 | 3/2013 | Hearn | |
| 2015/0142088 A1* | 5/2015 | Riva Godoy | A61F 7/03 607/108 |
| 2015/0223520 A1* | 8/2015 | Phillips | A61M 15/06 131/328 |
| 2016/0168438 A1* | 6/2016 | Harding | C09K 5/063 131/329 |
| 2017/0196262 A1* | 7/2017 | Brereton | A24F 47/006 |
| 2017/0231281 A1* | 8/2017 | Hatton | A24F 47/008 131/328 |

FOREIGN PATENT DOCUMENTS

| | | |
|---|---|---|
| AT | 321190 | 3/1975 |
| AT | 321191 | 3/1975 |
| AU | 2002364521 | 6/2003 |
| CA | 2146954 | 10/1996 |
| CA | 2414161 | 1/2002 |
| CA | 2414191 | 1/2002 |
| CA | 2520759 | 10/2004 |
| CA | 2492255 | 7/2006 |
| CA | 2668465 | 5/2009 |
| CA | 2641869 | 6/2010 |
| CH | 513656 | 10/1971 |
| CH | 698603 | 9/2009 |
| CN | 1038085 | 12/1989 |
| CN | 1043076 | 6/1990 |
| CN | 1045691 | 10/1990 |
| CN | 1059649 | 3/1992 |
| CN | 1123000 | 5/1996 |
| CN | 1123001 | 5/1996 |
| CN | 1126426 | 7/1996 |
| CN | 1158757 | 9/1997 |
| CN | 1287890 | 3/2001 |
| CN | 1293591 | 5/2001 |
| CN | 1293596 | 5/2001 |
| CN | 102212340 | 10/2001 |
| CN | 1578895 | 2/2005 |
| CN | 102131411 | 7/2011 |
| CN | 102499466 | 6/2012 |
| CN | 102604599 | 7/2012 |
| CN | 202351223 | 7/2012 |
| DE | 1100884 | 3/1961 |
| DE | 1425872 | 11/1968 |
| DE | 1290499 | 3/1969 |
| DE | 1813993 | 6/1970 |
| DE | 1425871 | 10/1970 |
| DE | 2315789 | 10/1973 |
| DE | 4105370 | 8/1992 |
| DE | 4307144 | 1/1995 |
| DE | 29509286 | 10/1995 |
| DE | 4420366 | 12/1995 |
| DE | 29700307 | 5/1997 |
| DE | 19854007 | 5/2000 |
| DE | 19854009 | 5/2000 |
| DE | 10058642 | 6/2001 |
| DE | 10007521 | 8/2001 |
| DE | 10064288 | 8/2001 |
| DE | 10164587 | 7/2003 |
| DE | 102005024803 | 6/2006 |
| DE | 102005023278 | 11/2006 |
| DE | 202006013439 | 11/2006 |
| DE | 102005056885 | 5/2007 |
| DE | 102006041544 | 8/2007 |
| DE | 102006041042 | 3/2008 |
| DE | 102006047146 | 4/2008 |
| DE | 102007011120 | 9/2008 |
| DE | 102008034509 | 4/2009 |
| DE | 102008013303 | 9/2009 |
| DE | 202009010400 | 12/2009 |
| DE | 102008038121 | 2/2010 |
| DE | 202010011436 | 12/2010 |
| DE | 102010046482 | 3/2012 |
| DK | 114399 | 6/1969 |
| DK | 488488 | 3/1989 |
| DK | 540774 | 7/1995 |
| DK | 540775 | 8/1997 |
| EP | 33668 | 8/1981 |
| EP | 0033668 | 8/1981 |
| EP | 0076897 | 4/1983 |
| EP | 0149997 | 7/1985 |
| EP | 0194257 | 9/1986 |
| EP | 0371285 | 6/1990 |
| EP | 0418464 | 3/1991 |
| EP | 0430559 | 12/1991 |
| EP | 0520231 | 12/1991 |
| EP | 0491952 | 7/1992 |
| EP | 0354661 | 4/1997 |
| EP | 540775 | 7/1997 |
| EP | 0824927 | 2/1998 |
| EP | 653218 | 9/1998 |
| EP | 1064083 | 1/2001 |
| EP | 1064101 | 1/2001 |
| EP | 1111191 | 6/2001 |
| EP | 1128741 | 9/2001 |
| EP | 1128742 | 9/2001 |
| EP | 1148905 | 10/2001 |
| EP | 2003997 | 10/2001 |
| EP | 1203189 | 5/2002 |
| EP | 1217320 | 6/2002 |
| EP | 1298993 | 4/2003 |
| EP | 1299499 | 4/2003 |
| EP | 1299500 | 4/2003 |
| EP | 1301152 | 4/2003 |
| EP | 1349601 | 10/2003 |
| EP | 1390112 | 2/2004 |
| EP | 1409051 | 4/2004 |
| EP | 1439876 | 7/2004 |
| EP | 1490452 | 12/2004 |
| EP | 1506792 | 2/2005 |
| EP | 1609376 | 12/2005 |
| EP | 1625334 | 2/2006 |
| EP | 1625335 | 2/2006 |
| EP | 1625336 | 2/2006 |
| EP | 1536703 | 9/2006 |
| EP | 1702639 | 9/2006 |
| EP | 1749548 | 2/2007 |
| EP | 1867357 | 12/2007 |
| EP | 1891867 | 2/2008 |
| EP | 1996880 | 12/2008 |
| EP | 2044967 | 4/2009 |
| EP | 2277398 | 7/2009 |
| EP | 2083642 | 8/2009 |
| EP | 2138058 | 12/2009 |
| EP | 2138059 | 12/2009 |
| EP | 2179229 | 4/2010 |
| EP | 2191735 | 6/2010 |
| EP | 2227973 | 9/2010 |
| EP | 2234508 | 10/2010 |
| EP | 2241203 | 10/2010 |
| EP | 2138057 | 11/2010 |
| EP | 2246086 | 11/2010 |
| EP | 2249669 | 11/2010 |
| EP | 2257195 | 12/2010 |
| EP | 2303043 | 4/2011 |
| EP | 2368449 | 9/2011 |
| EP | 2408494 | 1/2012 |
| EP | 2523752 | 11/2012 |
| EP | 2542131 | 1/2013 |
| ES | 262308 | 6/1982 |
| FR | 1418189 | 11/1965 |
| FR | 2573985 | 6/1986 |
| FR | 2604093 | 3/1988 |
| FR | 2700697 | 7/1994 |
| FR | 2730166 | 8/1996 |

(56) References Cited

FOREIGN PATENT DOCUMENTS

| | | |
|---|---|---|
| FR | 2818152 | 6/2002 |
| FR | 2842791 | 1/2005 |
| FR | 2873584 | 11/2006 |
| GB | 910166 | 11/1962 |
| GB | 922310 | 3/1963 |
| GB | 958867 | 5/1964 |
| GB | 1104214 | 2/1968 |
| GB | 1227333 | 4/1971 |
| GB | 1379688 | 1/1975 |
| GB | 1431334 | 4/1976 |
| GB | 2323033 | 9/1998 |
| GB | 2342874 | 4/2000 |
| GB | 2388040 | 11/2003 |
| GB | 2412326 | 9/2005 |
| GB | 2412876 | 10/2005 |
| GB | 2448478 | 10/2008 |
| GB | 2487851 | 8/2012 |
| IE | 63083 | 3/1995 |
| IT | 1289590 | 10/1998 |
| JP | 49061986 | 6/1974 |
| JP | 50096908 | 8/1975 |
| JP | 53014173 | 2/1978 |
| JP | 55094260 | 7/1980 |
| JP | 57110260 | 7/1982 |
| JP | 57177769 | 11/1982 |
| JP | 62205184 | 9/1987 |
| JP | 63153666 | 6/1988 |
| JP | 01191674 | 8/1989 |
| JP | 02-092986 | 4/1990 |
| JP | 02092986 | 4/1990 |
| JP | 02127493 | 5/1990 |
| JP | 03041185 | 2/1991 |
| JP | H 062164 | 1/1994 |
| JP | 2519658 | 7/1996 |
| JP | 08228751 | 9/1996 |
| JP | 3053426 | 10/1998 |
| JP | 11178562 | 7/1999 |
| JP | 3016586 | 3/2000 |
| JP | 2000119643 | 4/2000 |
| JP | 3078033 | 8/2000 |
| JP | 3118462 | 12/2000 |
| JP | 3118463 | 12/2000 |
| JP | 2002253593 | 9/2002 |
| JP | 2002336290 | 11/2002 |
| JP | 2003034785 | 2/2003 |
| JP | 2004504580 | 2/2004 |
| JP | 2005516647 | 6/2005 |
| JP | 2006219557 | 8/2006 |
| JP | 2007516015 | 6/2007 |
| JP | 2007522900 | 8/2007 |
| JP | 2008509907 | 4/2008 |
| JP | 2010526553 | 8/2010 |
| RU | 2066337 | 9/1996 |
| RU | 2098446 | 12/1997 |
| RU | 2285028 | 10/2006 |
| SE | 502503 | 10/2006 |
| WO | WO8601730 | 3/1986 |
| WO | WO9527411 | 10/1995 |
| WO | WO9805906 | 2/1998 |
| WO | WO9835552 | 8/1998 |
| WO | WO9914402 | 3/1999 |
| WO | WO9947273 | 9/1999 |
| WO | WO9947806 | 9/1999 |
| WO | WO9013326 | 11/1999 |
| WO | WO0028843 | 5/2000 |
| WO | WO0104548 | 1/2001 |
| WO | WO0140717 | 6/2001 |
| WO | WO0163183 | 8/2001 |
| WO | WO0205620 | 1/2002 |
| WO | WO0205640 | 1/2002 |
| WO | WO0206421 | 1/2002 |
| WO | WO0207656 | 1/2002 |
| WO | WO0224262 | 3/2002 |
| WO | WO02051466 | 7/2002 |
| WO | WO02096532 | 12/2002 |
| WO | WO03037412 | 5/2003 |
| WO | WO03049792 | 6/2003 |
| WO | WO03083007 | 10/2003 |
| WO | WO 2004/089126 A1 | 10/2004 |
| WO | WO2004098324 | 11/2004 |
| WO | WO2004104491 | 12/2004 |
| WO | WO2004104492 | 12/2004 |
| WO | WO2004104493 | 12/2004 |
| WO | WO2006022714 | 3/2006 |
| WO | WO2007054167 | 5/2007 |
| WO | WO2007078273 | 7/2007 |
| WO | WO2007090594 | 8/2007 |
| WO | WO2007098337 | 8/2007 |
| WO | WO2007116915 | 10/2007 |
| WO | WO2008015441 | 2/2008 |
| WO | WO2008051909 | 5/2008 |
| WO | WO2008069883 | 6/2008 |
| WO | WO2008151777 | 12/2008 |
| WO | WO2009006521 | 1/2009 |
| WO | WO2009042955 | 4/2009 |
| WO | WO2009079641 | 6/2009 |
| WO | WO2009092862 | 7/2009 |
| WO | WO2009118085 | 10/2009 |
| WO | WO2009152651 | 12/2009 |
| WO | WO2009155957 | 12/2009 |
| WO | WO2009156181 | 12/2009 |
| WO | WO2010017586 | 2/2010 |
| WO | WO2010047389 | 4/2010 |
| WO | WO2010053467 | 5/2010 |
| WO | WO2010060537 | 6/2010 |
| WO | WO2010102832 | 9/2010 |
| WO | WO2010107613 | 9/2010 |
| WO | WO2011045609 | 4/2011 |
| WO | WO2011088132 | 7/2011 |
| WO | WO2011101164 | 8/2011 |
| WO | WO201117580 | 9/2011 |
| WO | WO2011109304 | 9/2011 |
| WO | WO2012054973 | 5/2012 |
| WO | WO2012078865 | 6/2012 |
| WO | WO2012100430 | 8/2012 |

OTHER PUBLICATIONS

International Search Report and Written Opinion dated Jun. 30, 2014 for International Patent Application No. PCT/GB2013/052433 filed Sep. 18, 2013.
International Preliminary Report on Patentability dated Mar. 24, 2015 for International Patent Application No. PCT/GB2013/052433 filed Sep. 18, 2013.
International Search Report and Written Opinion dated Dec. 9, 2013 for International Patent Application No. PCT/EP2013/068797 filed Sep. 11, 2013.
International Preliminary Report on Patentability dated Mar. 31, 2015 for International Patent Application No. PCT/EP2013/068797 filed Sep. 11, 2013.
International Preliminary Report on Patentability dated Jun. 1, 2015 for International Patent Application No. PCT/EP2014/063785 filed Jun. 27, 2014.
International Search Report dated Oct. 30, 2014 for International Application No. PCT/EP2014/063785.
Application and File History for U.S. Appl. No. 14/428,344, filed Mar. 13, 2015, inventors Phillips et al.
International Search Report and Written Opinion for International Application No. PCT/EP2014/064365 dated Oct. 7, 2014.
International Search Report and Written Opinion for International Application No. PCT/EP2014/063785 dated Oct. 30, 2014.
Japanese Office Action, Application No. 2016-522550, dated Jan. 31, 2017, 4 pages (7 pages with translation).
Russian Office Action, Application No. 2016103729, dated Apr. 12, 2017, 12 pages (15 pages with translation).
Chinese Office Action, Application No. 201480037049.2, dated May 9, 2017, 23 pages (28 pages with translation).
Japanese Office Action, Application No. 2016-522550, dated Jul. 4, 2017, 4 pages ( 7 pages with translation).

(56) References Cited

OTHER PUBLICATIONS

Chinese Office Action, Application No. 201380047284.3, dated Nov. 13, 2017, 21 pages (30 pages with translation).
Japanese Office Action, Application No. 2017-017842, dated Dec. 1, 2017, 3 pages (6 pages with translation).
Japanese Office Action, Application No. 2016-522646, dated Dec. 15, 2016, 6 pages.

* cited by examiner

DEVICES COMPRISING A HEAT SOURCE MATERIAL AND ACTIVATION CHAMBERS FOR THE SAME

RELATED APPLICATIONS

The present application is a National Phase entry of PCT Application No. PCT/EP2014/063785, filed Jun. 27, 2014, which claims the benefit of GB Application No. 1311620.7, filed Jun. 28, 2013, each of which is incorporated herein by reference in its entirety.

FIELD

Embodiments relate to devices comprising a heat source material and configured to activate the heat source material.

BACKGROUND

Devices including a heat source material require a mechanism for activating the heat source on demand.

SUMMARY

According to a first aspect, a device is provided comprising: a heat source material which is a phase change material and which undergoes an exothermic phase change upon activation by an activating agent to generate heat; a heat source chamber within which the heat source material is held; an activation chamber providing the activating agent; and a barrier separating the interior of the heat source chamber from the interior of the activation chamber, wherein the activation chamber is deformable and wherein deformation of the activation chamber causes rupture of the barrier to allow contact between the activating agent and the heat source material.

In some embodiments, the device may further comprise a housing within which the heat source and activation chambers are located, and wherein the activation chamber is deformable by applying pressure to a deformable portion of the housing.

In some embodiments, any deformation of the heat source chamber caused by a user applying manual pressure to said chamber will not cause rupture of the barrier.

In some embodiments, the activation chamber may comprise a deformable body forming a chamber having an opening which is sealed by the barrier.

In some embodiments, the body of the activation chamber may be shaped to facilitate rupture of the barrier upon deformation.

In some embodiments, the body of the activation chamber may comprise an internal protrusion which facilitates rupture of the barrier when the body is deformed.

In some embodiments, the heat source chamber may have an opening which is aligned with an opening of the activation chamber and both openings are sealed by a barrier.

In some embodiments, the phase change material may be sodium acetate trihydrate.

In some embodiments, the activating agent may be a solid material.

In some embodiments where the heat source material is sodium acetate trihydrate, the activating agent may comprise a sodium acetate crystal or a sodium acetate trihydrate crystal.

In some embodiments, the device further includes a nicotine source which releases nicotine upon being heated by the heat source material. The nicotine source may comprise tobacco.

According to a second aspect, an activation chamber is provided for use in a device according to an embodiment of the first aspect, the activation chamber comprising an activating agent to trigger activation of a heat source material.

In some embodiments the activation chamber is a blister.

In some embodiments, the activating agent is provided in the form of a powder, tablet or in a monolithic form.

In some embodiments, the activating agent is provided as a layer or coating on or in the activation chamber.

BRIEF DESCRIPTION OF THE DRAWINGS

For the purposes of example only, embodiments are described below with reference to the accompanying drawings, in which.

DETAILED DESCRIPTION

Embodiments relate to a simple, small and reliable mechanism for activating a heat source material to initiate the generation of heat. Such a mechanism may be incorporated into a device including a heat source and optionally other elements.

A heat source material is a material which will emit heat when activated. The material may be a phase change material which undergoes a phase change upon activation and thereby releases heat. For example, the material may be a super-cooled phase change material.

Various devices may include a heat source. For example, packaging or containers for food and drink products may include a heat source so that contents may be heated "on the move." Such containers may include the food or drink, or these may be introduced into the container prior to activating the heat source.

Other devices may be used to heat medical supplies to a target temperature before use.

A heat source material may be included in non-combustible smoking articles. These may include devices which heat a nicotine-containing compound, such as tobacco, to trigger the release of nicotine without generating smoke from the combustion of tobacco. In such devices, a heat source is required which will heat the nicotine-containing compound on demand and will quickly and reliably heat the nicotine-containing compound in a predictable way (i.e., over a known period and to a known temperature).

In all of the aforementioned devices and in other examples of devices including a heat source, it is important to be able to control the activation of the heat source. What is more, it is important to be able to reliably and quickly trigger the heat source when desired.

The heat source material and the activating agent are stored separately within the devices. The heat source material is held in a heat source chamber whilst the activating agent is provided by the activation chamber. The interiors of these chambers are separated by a barrier. When the heat source material is to be triggered, the barrier is ruptured to allow contact between the heat source material and the activating agent.

In some embodiments, the heat source material is phase change material which emits heat upon undergoing a phase change.

There are several classes of phase change materials (PCMs). Suitable PCMs should exhibit stability as a supercooled fluid at room temperature and/or at the possible storage temperatures. In addition, the PCMs should be readily and reliably activated by contact with an activating agent. In some embodiments, the phase change is from liquid to solid, although other types of phase change materials may be used.

In some embodiments, the heat source material included in the device is a hydrated salt PCM. Suitable hydrated salts include sodium acetate trihydrate, sodium hydroxide monohydrate, barium hydroxide octahydrate, magnesium nitrate hexahydrate and magnesium chloride hexahydrate. In some embodiments which may be advantageous, the heat source material is sodium acetate trihydrate. It is stable at room temperature and is non-hazardous. The phase change of sodium acetate trihydrate from liquid to solid can also be reliably and quickly initiated by a variety of activating agents at least some of which can be incorporated into a separate chamber and transferred into contact with the heat source material.

Nucleation is the process by which the phase change of the PCM from liquid to solid is initiated and it may be classed as either heterogeneous or homogeneous nucleation. In heterogeneous nucleation, an insoluble foreign body, such as a dust particle or a feature on the wall of the container holding the PCM, acts as the centre upon which the first ions or molecules become attached and oriented, rapidly attracting additional entities to form a solid crystal. In homogeneous nucleation, a few ions or molecules arrive stochastically into the correct orientation in the course of their random movement through the bulk of the liquid phase, providing a site which then attracts additional ions or molecules and hence forms a growing solid crystal entity.

The introduction of a solid crystalline entity, such as a small crystal of sodium acetate, (a so-called "seed" crystal) into the bulk of the liquid phase immediately provides a very large number of sites which will attract ions or molecules from the bulk liquid phase. The introduction of a seed crystal into a super-cooled system thus accelerates the crystallization process by eliminating the need for random molecular interactions.

In some embodiments where the heat source material is sodium acetate trihydrate, the activating agent may include one or more of the following: solid sodium acetate or solid sodium acetate trihydrate. In some embodiments, the solid form may comprise, for example, one or more crystals, a coating or layer, powder, granules or a monolithic form, such as a molded or pressed tablet or similar form. In some embodiments, the solid form may be formed by allowing a relatively small volume of liquid SAT crystallize to form a monolithic form.

In some embodiments, an activating agent, such as one comprising sodium acetate or sodium acetate trihydrate in a solid form, may be provided in the form of a pressed, molded or printed monolithic form, such as a tablet or other solid form suitable for inclusion in the activation chamber as described herein. In some embodiments, a solid monolithic form of sodium acetate trihydrate may be formed in situ within the activation chamber. The activation chamber may be formed and filled with the sodium acetate trihydrate in an unstable liquid form. This unstable liquid will then solidify within the activation chamber, forming a solid mass which may be used to trigger a phase change in a supercooled liquid SAT heat source material. What is more, the solid mass will also be capable of transmitting pressure from the deformation of the activation chamber body to the barrier to facilitate its rupture.

In some embodiments, it is desirable to select an activating agent which is stable and, in some embodiments, is stable when exposed to elevated temperatures, for example during the forming and sealing of the activation chamber in which it is to be stored.

In some embodiments, the activating agent may be a solid comprising one or more of a salt, for example, common salt NaCl, Chalk ($CaCO_3$), and a cellulose derivative, for example, Carboxymethyl Cellulose (CMC). The solid may comprise, for example, one or more crystals, a coating or layer, powder, granules or a monolithic form, such as a molded or pressed tablet or similar form.

In some embodiments, the activating agent may comprise a solid non-hygroscopic material, for example, metal filings such as iron, copper, aluminum or stainless steel filings. A potential advantage of using a solid non-hygroscopic material rather than a solid hygroscopic material as the activating agent is that a solid non-hygroscopic material is less prone to liquefying in the event that moisture enters the activation chamber 4.

In embodiments, the heat source material 3 and the activating agent 5 are stored separately in the device 1 so that the chance of accidental activation is minimized. The two components are stored in separate chambers and are separated by a barrier. The heat source chamber 2 holds the heat source material 3 and the activation chamber 4 provides the activating agent 5. The barrier 6 preventing the activating agent 5 from contacting the heat source material 3 before such contact is desired is a rupturable film and is configured to allow the activating agent 5 provided by the activation chamber 4 to come into contact with the heat source material 3 so that the heat source is activated and heat is generated.

In some embodiments, contact between the activating agent 5 and the heat source material 3 may be as a result of the activating agent being displaced through the ruptured barrier 6 and into the heat source chamber 2. This displacement may, for example, be as a result of the deformation of the activating chamber. Alternatively or in addition, following rupture of the barrier, there may be displacement of the heat source material 3 out of the heat source chamber 2 and into the activation chamber 4, so that the heat source material 3 and the activating agent 5 come into contact.

The rupture of the barrier 6 is achieved by deforming the activation chamber 4. In some embodiments, the deformation of the activation chamber 4 additionally causes displacement of the activating agent 5 so that it may contact the heat source material.

In some embodiments, the activation chamber 4 is deformed upon the application of manual pressure by a user. This pressure may be applied directly, for example by the user pressing on the device 1 with a digit. Thus, in some embodiments, the user may apply the pressure directly onto the surface of the activation chamber 4, by pressing directly on the body of the activation chamber 4. The digit may either be in direct contact with the outer surface of the activation chamber 4 or it may be in contact with a deformable section of housing which is in contact with or otherwise transmits the pressure to the activation chamber.

Alternatively, the pressure may be applied indirectly, for example with the pressure being transmitted by a mechanical means. Thus, in some embodiments, the device further comprises an actuating mechanism by which the user deforms the activation chamber 4. In some embodiments, the actuating mechanism may comprise a button, optionally a spring-loaded and/or sliding button. Various other types of actuating mechanisms are also envisaged, including a plunger or a lever. In some embodiments, for example, the actuating mechanism may be configured to be depressed, pulled, twisted or squeezed to deform the activation chamber 4. In the embodiment illustrated in FIG. 3, the device includes a housing 11 with a deformable portion 12 which surrounds both the heat source chamber 2 and activation chamber 4. The activation chamber 4 is surrounded by a housing at least a portion of which 12 is deformable so that manual pressure applied by the user on the deformable portion of the housing 12 is transmitted to the body of the activation chamber 4 to deform it.

In some embodiments, the heat source chamber 2 is generally not deformable upon application of manually applied pressure, i.e., the heat source chamber 2 is rigid. In other embodiments, the heat source chamber may be deformable but may not be deformable in a manner or to an extent that will or is likely to cause the rupture of the rupturable barrier. In some embodiments that may be advantageous in certain circumstances, the rupturable barrier may only be ruptured as a result of deformation of the activation chamber.

In some embodiments, the device 10 includes a housing 11 which includes a deformable portion 12 aligned with the activation chamber 4 to allow the transmission of pressure from the external surface of the deformable portion 12 of the housing 11 to the activation chamber 4 to allow deformation of the chamber 4, rupture of the barrier 6 and, optionally, displacement of the activating agent 5 stored within the activation chamber 4 through the barrier 6. In some embodiments, the rest of the housing 11 (aside from the deformable portion 12 aligned with the activation chamber 4) may be generally a rigid structure. In some embodiments, portions of the housing 11 may be provided with sufficient rigidity for them to provide a reaction surface against which the deformable parts of the device, for example the deformable activation chamber 4 may be pressed. This may assist in enabling the pressure applied to the activation chamber 4 to cause deformation of at least a part of the activation chamber 4 and the consequent rupture of the barrier 6.

Figure 1:
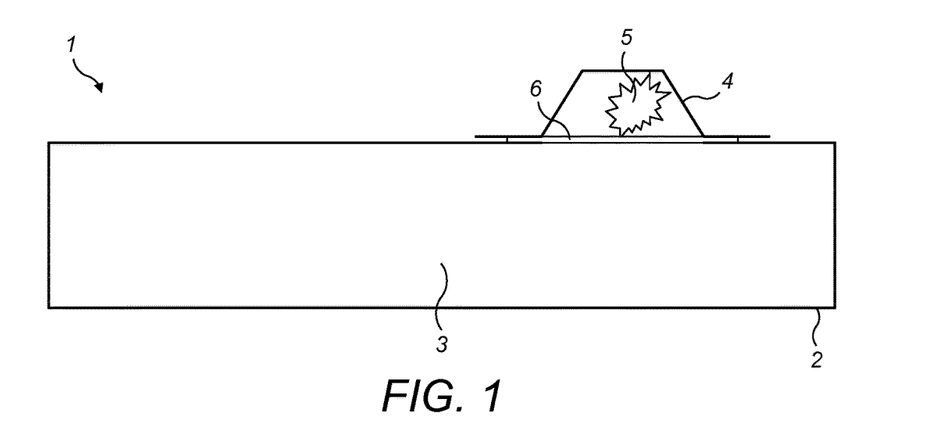
FIG. 1 is a schematic illustration of a device according to one possible embodiment.
Figure 2:
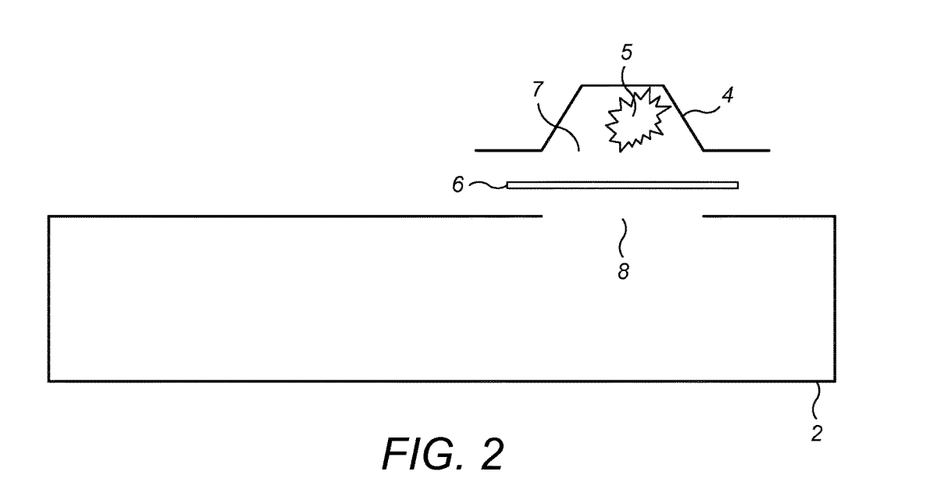
FIG. 2 is a schematic illustration of an exploded view of the device illustrated in FIG. 1.
Figure 3:
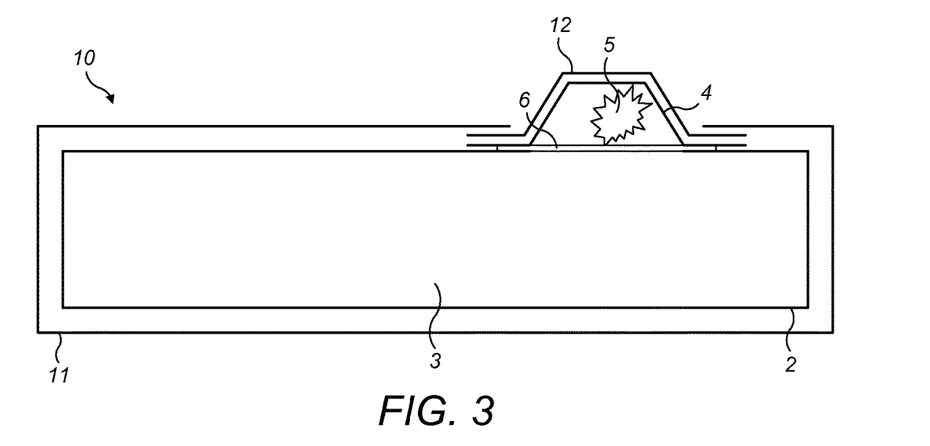
FIG. 3 is a schematic illustration of a device according to an alternative embodiment.

As shown in FIGS. 1 to 3, the device 1, 10 may be configured so that the activation chamber 4 is directly adjacent to the heat source chamber 2 so that the activating agent and the heat source material may come into contact with one another once the barrier 6 separating them has been ruptured. In such embodiments, an opening 8 in the heat source chamber 2, the rupturable barrier 6 and an opening 7 in the activation chamber 4 may all be aligned. In alternative embodiments (which are not illustrated), there may be a further chamber or passage into or through which the activating agent and/or heat source material pass in order to come into contact with each other and initiate heat generation.

In some embodiments, the activation chamber 4 suitable for use in embodiments may comprise a deformable body which transmits the pressure applied to the activation chamber, and a barrier which is ruptured, preferably in a predetermined and predicable manner, when the body is deformed. In some embodiments, the activation chamber comprises an activating agent held within the chamber. In other embodiments, the activating agent may be provided as an integral part of the activation chamber, for example in the form of a layer or coating. This layer or coating may, for example, be provided on an internally facing surface of the activation chamber 4, such as the internal surface of the deformable body and/or the internal surface of the barrier.

In some embodiments, the activation chamber may comprise a laminate, either forming the deformable body or part thereof, or forming the barrier. In some of these embodiments, the laminate may include a layer comprising the activating agent. This activating agent layer may be located on the surface of the laminate which is inside the activation chamber prior to deformation of the chamber and rupture of the barrier. Alternatively or in addition, the layer of activating agent may be within the multi-layer laminate structure so that it is not exposed until the laminate is torn or ruptures.

In some embodiments, the activating agent provided in such a layer or coating may be displaced by the deformation of the activation chamber 4 to the extent that the activating agent extends into the heat source chamber 2.

In some embodiments, the activating agent 5 may remain in the activation chamber following deformation of the activation chamber and then, in order for there to be contact between the activating agent and the heat source material, it may be necessary for the heat source material to enter the activation chamber 4.

Where it is desirable or necessary for the heat source material to enter the activation chamber following rupture of the rupturable barrier, this may be encouraged by the creation of a region of relatively low pressure in the activation chamber. In one possible embodiment, the activation chamber may have a lower internal pressure than the heat source chamber when it is sealed. When the rupturable barrier is then ruptured, the heat source material from the adjacent heat source chamber is drawn into the activation chamber. Alternatively or in addition, the activation chamber may be configured to create a region of relatively low pressure following rupture of the rupturable barrier. For example, the activation chamber may be formed from a resiliently deformable material so that, following deformation of the body of the chamber to cause rupture of the barrier, the body of the chamber will revert to its original form, thereby drawing the heat source material from the adjacent heat source chamber into the activation chamber.

Alternatively or in addition, the heat source material may be encouraged to enter the activation chamber by capillary action. The activation chamber may be shaped to draw the heat source material into it by capillary action when the barrier is ruptured.

Where it is desirable or necessary for the activating agent to exit the activation chamber following rupture of the rupturable barrier, this may be encouraged by the creation of a region of relatively high pressure in the activation chamber. In one possible embodiment, the activation chamber may have a higher internal pressure than the heat source chamber when it is sealed. When the rupturable barrier is then ruptured, the activating agent may be expelled from the activation chamber into the adjacent heat source chamber.

According to some embodiments, the activation chamber in which the activating agent is stored is a blister or a blister-like element. As used herein, the term "blister" refers to a structure such as is found in a blister pack or bubble pack. Such packs are examples of pre-formed packaging used for small consumer goods, foods, and pharmaceuticals.

As used herein, the blister comprises a body forming a chamber, the body being made from a material such as, for example, a thermoformed plastic. The chamber has an opening which is closed by a barrier layer which may be attached to the body, for example around the opening. The barrier layer may be adhered to the body by any suitable means. In some embodiments, the barrier layer is film, foil, membrane or plastic sheet material. In some embodiments, the barrier layer ruptures by physically breaking or tearing under the pressure exerted on it. Alternatively or in addition, in some embodiments, it may be the seal between the body and the barrier layer which ruptures, so that the barrier layer and body become separated, thereby at least partially exposing the previously sealed opening.

In some embodiments, the body of the activation chamber and the barrier may be formed from the same or similar materials. For example, in some embodiments, the body and barrier may be formed from a plastic material (such as, for example, polyvinyl chloride, optionally laminated with polychlorotrifluoroethylene, or multi-layer materials comprising cyclic olefin copolymers or polymers, polypropylene, polyethylene, or glycol-modified polyethylene terephthalate), or a foil (such as, for example, an aluminum-based foil, including aluminum-containing laminates). In some embodiments, the body of the activation chamber and the barrier may be made of a water resistant material in order to reduce the likelihood of moisture reaching the activating agent. For example, the barrier layer could be made of cold-formed aluminum or from polyvinylidene chloride (PVDC). In some embodiments, the rupturable portion of the activation chamber may comprise or consist of a local weakening of the material, for example by locally adjusting the thickness of the material.

Figure 4:
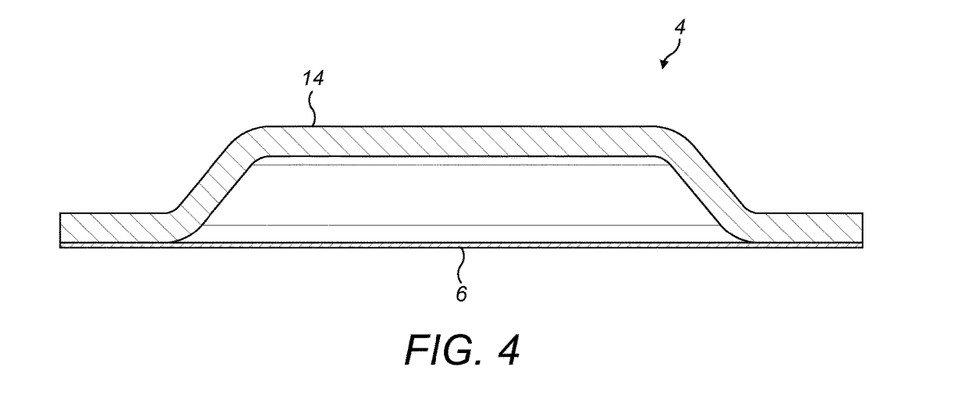
FIG. 4 is a cross-sectional view of an embodiment of the activation chamber.
Figure 5:
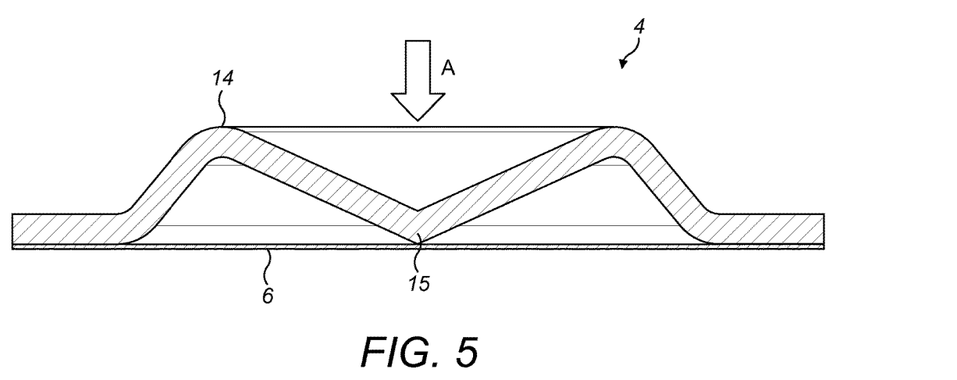
FIG. 5 is a cross-sectional view of an alternative embodiment of the activation chamber.

Illustrative examples of activation chambers in the form of blisters are shown in FIGS. 4 and 5. The activation chamber 4 may comprise a body 14 formed from a deformable material and having an opening 7 which is sealed by a barrier 6 with the activating agent (not shown) located within the chamber. In some embodiments, the body 14 of the activation chamber 4 may be formed from a plastic or other deformable material. In alternative embodiments, the body 14 of the activation chamber could be formed from a second foil layer, for example comprising a foil laminate. The body of the activation chamber is configured to deform when a user applies manual pressure directly or indirectly to the surface of the activation chamber. The extent to which the body of the activation chamber deforms in response to pressure will be dependent, at least to an extent, upon the material of the body, its thickness and the shape of the body.

In some embodiments, the barrier 6 is attached to the body 14 of the activation chamber 4 in order to seal the opening 7. This may be achieved by attaching the barrier to the body of the activation chamber, for example around the opening. This attachment may, for example, be achieved by fusion or welding of the materials of the barrier and the body, or by using an adhesive. Sealing the activation chamber 4 by attaching the rupturable barrier 6 to the body 14 has the advantage that the whole activation chamber, including the activating agent, may be formed and supplied as a separate component and easily added to the other components of the device.

In alternative embodiments, the activation chamber may be sealed by a rupturable barrier which is not attached to the body of the activation chamber. For example, the body of the activation chamber may be sealed as a result of the opening of the body being aligned with and abutting another component of the device. In some embodiments, the opening of the activation chamber may abut a rupturable barrier which is attached to and/or forms part of another component of the device, such as the heat source chamber. Such an arrangement would mean that the contents of the activation chamber cannot exit without rupture of the barrier. This arrangement also allows the deformation of the activation chamber to apply sufficient force to the barrier to rupture it.

In some embodiments, the body of the heat source chamber has an opening which is sealed by a rupturable barrier. This may be achieved by attaching the barrier to the body of the heat source chamber, for example around the opening. This attachment may, for example, be achieved by fusion or welding of the materials of the barrier and the body, or using an adhesive. Sealing the heat source chamber by attaching the rupturable barrier to the body has the advantage that the whole heat source chamber including the heat source material may be formed and supplied as a separate component and therefore easily added to the other components of the device.

In some embodiments, both the heat source and activation chambers are individually sealed by a rupturable barrier. The barriers and the openings of the chambers that they respectively seal can be aligned within the device to allow the deformation of the activation chamber to cause rupture of both barriers to allow contact between the activating agent and the heat source material.

The rupture of the barrier 6 is caused by the deformation of the activation chamber 4. In some embodiments, deformation of the chamber will increase the pressure within the sealed chamber forcing the container to rupture or burst at a weak point which will generally be the rupturable barrier or a point at which the barrier is attached to a chamber body. In some embodiments, the activating agent held within the activation chamber is a solid material. Upon deformation of the activation chamber, the solid activating agent may become pressed against the rupturable barrier, thereby transmitting and focusing the force applied to the body of the activation chamber and facilitating rupture. Once the barrier has ruptured, the activating agent will, at least partially, pass through the ruptured barrier and out of the activation chamber.

In the embodiment illustrated in FIG. 1, the activating agent 5 is a solid material which may be forced through the barrier 6. Upon deformation of the activation chamber 4, the activating agent 5 is pressed against the barrier 6. Eventually, the force exerted on the barrier 6 by the activating agent 5 will cause the barrier 6 to rupture. This release of the resistance to the applied pressure will cause at least part of the activating agent to be pushed through the ruptured barrier and into the heat source chamber 2 and into contact with the heat source material.

In some embodiments, the activation chamber may include additional or alternative means for focusing the force applied to the rupturable barrier as a result of the activation chamber being deformed. The activation chamber may include a protrusion which contacts the rupturable barrier upon deformation of the activation chamber. If the protrusion contacts the barrier over a relatively small surface area, the force applied to the barrier will be focused and this will facilitate rupture. One embodiment including such a protrusion is illustrated in FIG. 5. The activation chamber 4 has a body 14 which is shaped to include a protrusion 15. When the body 14 is deformed by application of pressure, as indicated by the arrow A, the protrusion 15 formed on the inner surface of the body 14 comes into contact with the barrier 6 and focuses the force applied by the deformation and displacement of the shaped portion of the activation chamber body onto a local area of the barrier, facilitating rupture. A similar effect could be achieved by providing protrusions which are held within the activation chamber but which are not an integral part of it. Thus, one or more solid shaped articles could be included with the activating agent in the activation chamber 4, and these articles would be pressed against the barrier upon deformation of the activation chamber to facilitate rupture. Such shaped articles could be provided with sharp edges, points or the like to ensure that they facilitate rupture of the barrier. In some embodiments, the shaped articles have a shape which ensures that, whatever the orientation of the shaped article within the activation chamber, the pressure applied to the outer surface of the chamber is focused onto a relatively small area of the rupturable barrier, in order to facilitate rupture.

In some embodiments where shaped articles are provided with sharp edges, points or the like to facilitate rupture of the barrier, the sharp edges or points may also activate the heat source material upon contact therewith, for example by providing nucleation sites. Alternatively or in addition, where shaped articles are provided to facilitate rupture of the barrier (either with or without sharp edges), these articles may have roughened surfaces which can provide a large number of nucleation sites to activate the heat source material upon contact therewith.

In some particular embodiments, the means or articles, including those discussed above, for focusing the force applied to the rupturable barrier may comprise a coating or layer comprising an activating agent.

In some embodiments, the barrier 6 is able to re-seal itself after having been ruptured. For example, the barrier 6 may comprise a layer of resilient material the resilience of which causes the layer to reseal after having been ruptured. Such a barrier 6 may be in the form of a rubber septum. In some such embodiments, the activation chamber 4 may be provided with one or more sharp protrusions which are brought into contact with and rupture the barrier 6 when the activation chamber 4 is deformed under pressure applied by a user. The one or more sharp protrusions may activate the heat source material upon contact with it. The one or more sharp protrusions may comprise a metal, for example, iron, copper, aluminum or stainless steel. The activation chamber 4 itself may be resilient so that it regains its original shape when pressure ceases to be applied to it so that the one or more protrusions are withdrawn from the barrier 6 which then re-seals itself. Accordingly, in some embodiments, the activation chamber 4 is re-usable.

In some embodiments, the barrier may be constructed to ensure that, upon rupture, the ruptured barrier has sharp edges which may activate the heat source material upon contact therewith, for example by providing nucleation surfaces. Alternatively or in addition, the means provided to rupture the barrier may be configured to ensure that, upon rupture, the ruptured barrier has sharp edges which may activate the heat source material upon contact therewith, for example by providing nucleation surfaces. The sharp edges may be capable of activating the heat source material and so, in some embodiments, these sharp edges of the barrier formed upon rupture are the activating agent and it may not be necessary for any other activating agent to be present.

Figure 6:
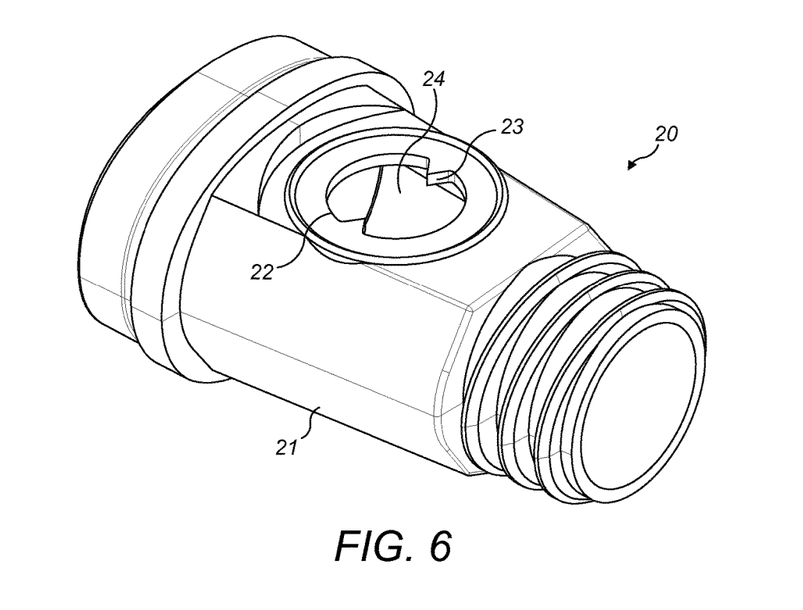
FIG. 6 is a schematic illustration of a section of housing of a device according to one possible embodiment.
Figure 7:
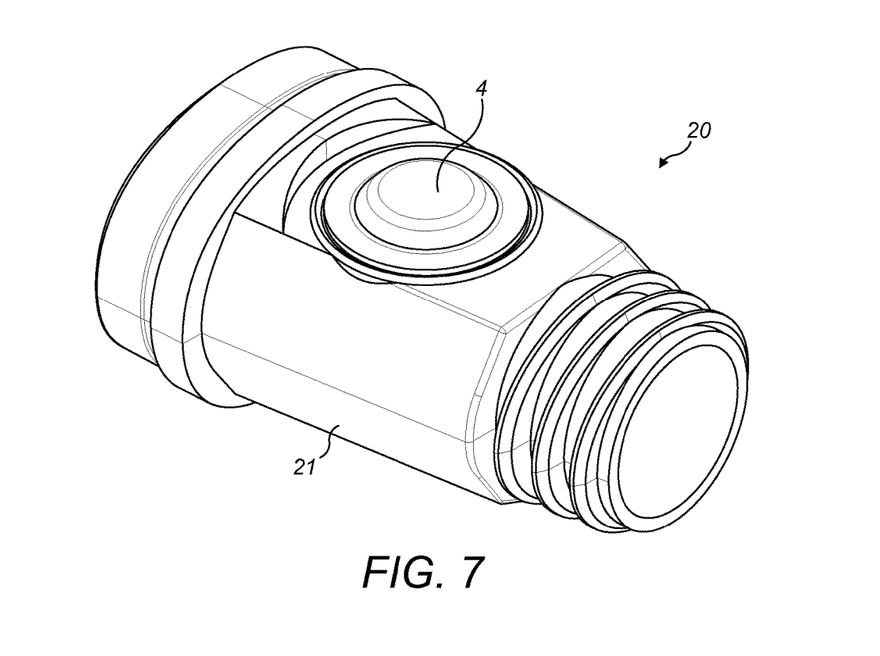
FIG. 7 is a schematic illustration of a section of housing of a device including an activation chamber according to one possible embodiment.

In yet further embodiments, other parts of the device may include means for facilitating rupture of the barrier upon deformation of the activation chamber. FIG. 6 shows a possible configuration of a housing part 20 which is configured to receive and hold the activation chamber 4. The activation chamber 4 may, for example, be a blister along the lines described above. The housing part 20 has a body 21 which includes a lip 22 surrounding an opening 24 into which one or more protrusions 23 radially extend. When incorporated into the device, the activation chamber blister sits on the lip 22 of the housing body 21, so that the barrier spans the opening 24 and rests upon the lip 22 with the protrusion(s) 23, as shown in FIG. 7. Upon deformation of the activation chamber 4, the chamber, and in particular the barrier 6, is pushed against the lip 22 and the protrusions 23. The pressure can facilitate rupture of the barrier at the points at which the protrusions 23 contact the barrier 6. The housing part 20, and in particular the lip 22, provides a reaction surface against which the activation chamber may be pressed to ensure that it deforms upon application of pressure, so as to rupture the rupturable barrier.

In alternative embodiments, the activation chamber 4 and heat source chamber 2 are positioned adjacent to one another and in abutment, and the heat source chamber may be provided with protrusions or the like to facilitate rupture of the barrier 6 upon deforming the activation chamber 4. In some embodiments, the heat source chamber may provide a reaction surface against which the activation chamber may be pressed to ensure that it deforms upon application of pressure, so as to rupture the rupturable barrier.

The barrier is selected from a material which will rupture when placed under the types of pressure the device is designed to transmit from a user manually actuating the device. The barrier may be a film or membrane. The material will be selected to provide the requisite strength and rupturability. For example, the material and thickness of the barrier is selected to rupture or tear based on the degree and direction of force which may be applied (directly or indirectly) by the user to the surface of the activation chamber. In addition, it is important that the barrier material is inert with respect to the materials it is in contact with during storage and use. In some embodiments the barrier may be provided with pre-weakened areas to facilitate rupture. In some embodiments, the barrier may be a foil, film, membrane or sheet. In other embodiments, the rupturable barrier may be a pre-weakened portion of the body of the activation chamber.

In certain embodiments, the physical size or volume of the activating agent 5 will be significantly smaller than the size or volume of the heat source material 3. As a result, it may be desirable for the activation chamber 4 to be as small and/or slim as possible, so that it does not substantially dictate the size and/or shape of the device. In some embodiments, therefore, due to the constrained geometry of such a device 1, the size and shape of the activation chamber 4 holding the activating agent 5 may be optimized to ensure the rupturable barrier 6 ruptures with only a small deformation of the body of the activation chamber 4. A slim configuration of a blister-like activation chamber 4 is illustrated in FIGS. 4 and 5, where it can be seen that the application of pressure by a user on the body 14 of the activation chamber 4 as indicated by the arrow A does not need to deform the body 14 very much before the contents of the chamber (not shown) and/or a protrusion 15 contact the barrier 6 and apply a rupturing pressure.

In some embodiments, the external dimensions of the activation chamber include: a diameter of between about 2 to about 10 mm, between about 5 to about 9 mm, between about 6 to about 8 mm or a diameter of about 7 mm; and a depth of between about 0.4 and 5 mm, between about 0.7 to about 3 mm, between about 1 mm to about 2 mm, or a depth of about 1 mm.

In some specific embodiments, the device is an inhalation device configured to heat a heatable material to volatilize at least one component of the heatable material to form an inhalable vapor. As used herein, the term 'heatable material' includes any material that provides volatilize components upon heating.

In some embodiments, the inhalation device is a nicotine delivery system. In such embodiments, the heatable material may comprise a source of nicotine. In some embodiments, the heatable material may include any tobacco-containing material and may, for example, include one or more of tobacco, tobacco derivatives, tobacco extracts, treated or modified tobacco such as expanded tobacco and reconstituted tobacco, or tobacco substitutes. For the avoidance of doubt, in the context of the present invention, the heatable material is not combusted and smoke is not generated. Nevertheless, the heatable material does provide a source of components which are volatilize upon use and are to be inhaled by the user.

Figure 8:
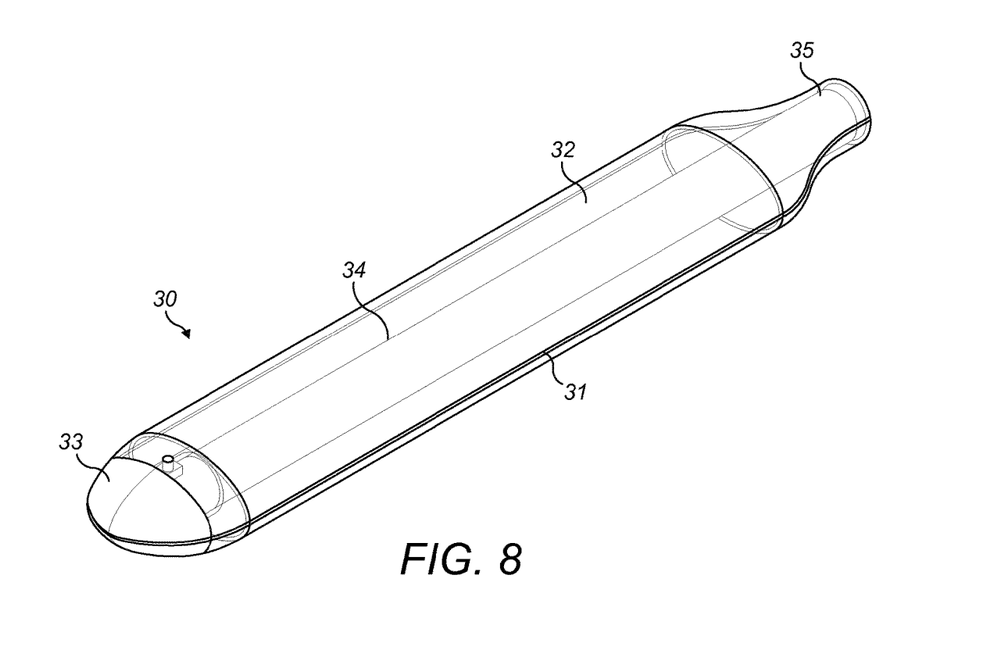
FIG. 8 is a schematic illustration of an inhalation device including a heatable material.

In some embodiments, as illustrated in FIG. 8, such an inhalation device 30 comprises a housing 31 within which the heat source material 32 is held in a heat source chamber, and a heatable material 34 is held in a separate heating chamber, the heat source chamber and the heating chamber being arranged to allow transfer of heat from the heat source chamber to the heatable material, so that at least one component of the heatable material may be volatilize. The device further includes an activation chamber holding an activating agent which may be displaced from the activation chamber to the heat source chamber upon deforming the activation chamber by applying pressure to a deformable portion 33 of the housing. The activation chamber and the activation process may be as described above. In some embodiments, the inhalation device additionally includes a mouthpiece 35 through which the volatilized component(s) may be inhaled.

In order to address various issues and advance the art, the entirety of this disclosure shows by way of illustration various embodiments in which that which is claimed may be practiced and provide for superior devices for initiating a heat source material and methods of manufacturing and using the same. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. A heating device comprising:
   a heat source material which is a phase change material and which undergoes an exothermic phase change upon activation by an activating agent to generate heat;
   a heat source chamber within which the heat source material is held;
   an activation chamber providing the activating agent;
   a barrier separating the interior of the heat source chamber from the interior of the activation chamber, wherein the activation chamber is deformable and wherein deformation of the activation chamber causes rupture of the barrier to allow contact between the activating agent and the heat source material, the contact activating the exothermic phase change of the phase change material, and
   a housing to receive a nicotine source arranged to release nicotine upon being heated by the generated heat.

2. The heating device as claimed in claim 1, wherein the heat source chamber and the activation chamber are located in the housing, and wherein the activation chamber is deformable by a user applying manual pressure to a deformable portion of the housing.

3. The heating device as claimed in claim 1, wherein the heat source chamber is deformable by a user applying manual pressure to the heat source chamber and is arranged so that any deformation of the heat source chamber caused by a user applying manual pressure to the chamber will not cause rupture of the barrier.

4. The heating device as claimed in claim 1, wherein the activation chamber comprises a deformable body having an opening which is sealed by the barrier.

5. The heating device as claimed in claim 1, wherein the activation chamber is shaped to facilitate rupture of the barrier upon deformation of the activation chamber.

6. The heating device as claimed in claim 1, wherein the activation chamber comprises an internal protrusion which facilitates rupture of the barrier when the activation chamber is deformed.

7. The heating device as claimed in claim 1, wherein the heat source chamber has an opening which is aligned with an opening of the activation chamber and both openings are sealed by the barrier.

8. The heating device as claimed in claim 1, wherein the phase change material is a formulation comprising sodium acetate trihydrate.

9. The heating device as claimed in claim 1, wherein the activating agent is a solid material.

10. The heating device as claimed in claim 8, wherein the activating agent comprises solid sodium acetate or solid sodium acetate trihydrate.

11. The heating device as claimed in claim 1, wherein the activating agent is a solid and comprises one or more of a salt, chalk, or a cellulose derivative.

12. The heating device as claimed in claim 1, wherein the activating agent comprises a solid non-hygroscopic material.

13. The heating device as claimed in claim 12, wherein the activating agent comprises metal filings.

14. The heating device as claimed in claim 1, wherein the barrier comprises a layer of resilient material, wherein the resilience of the layer causes the layer to re-seal after rupturing.

15. The heating device as claimed in claim 1, wherein the nicotine source comprises tobacco.

16. An activation chamber for use in the heating device as claimed in claim 1, the activation chamber comprising the activating agent to trigger activation of the heat source material.

17. The activation chamber as claimed in claim 16, wherein the activation chamber is a blister.

18. The activation chamber as claimed in claim 16, wherein the activating agent is provided in the form of a powder, a tablet, or in a monolithic form.

19. The activation chamber as claimed in claim 16, wherein the activating agent is provided as a layer or a coating on the activation chamber.

20. The activation chamber as claimed in claim 16, wherein the activating agent is provided as a layer or a coating in the activation chamber.

\* \* \* \* \*